United States Patent (10) Patent No.: US 8,518,008 B2
Yoshioka et al. (45) Date of Patent: Aug. 27, 2013

(54) DISPOSABLE DIAPER

(75) Inventors: Toshiyasu Yoshioka, Kanonji (JP);
Yoshio Ono, Kanonji (JP); Shunsuke Masaki, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/289,398

(22) Filed: Nov. 4, 2011

(65) Prior Publication Data

US 2012/0116343 A1 May 10, 2012

(30) Foreign Application Priority Data

Nov. 5, 2010 (GB) .................................. 1018715.1

(51) Int. Cl.
*A61F 13/15* (2006.01)

(52) U.S. Cl.
USPC .............. 604/385.29; 604/385.3; 604/385.24

(58) Field of Classification Search
USPC ............. 604/385.24, 385.3, 394, 393, 385.29
See application file for complete search history.

(56) References Cited

U.S. PATENT DOCUMENTS

| | | | |
|---|---|---|---|
| 5,749,865 A | 5/1998 | Yamamoto et al. | |
| 6,375,646 B1 * | 4/2002 | Widlund et al. | 604/385.3 |
| 2007/0073262 A1 * | 3/2007 | Babusik et al. | 604/396 |
| 2010/0106123 A1 * | 4/2010 | Fukae | 604/373 |

FOREIGN PATENT DOCUMENTS

| | | |
|---|---|---|
| EP | 0753292 A2 | 1/1997 |
| EP | 2327384 A1 | 6/2011 |
| EP | 2377500 A1 | 10/2011 |
| JP | 2007-029482 A | 2/2007 |
| JP | 2007509725 A | 4/2007 |
| JP | 2009125087 A | 6/2009 |
| JP | 2010068989 A | 4/2010 |
| WO | 2005051263 A1 | 6/2005 |
| WO | 2010032581 A1 | 3/2010 |
| WO | 2010074131 A1 | 7/2010 |

OTHER PUBLICATIONS

British Search Report for 1018715.1 dated Feb. 1, 2011.
ISR for PCT/JP2011/075501 dated Jan. 24, 2012.

* cited by examiner

*Primary Examiner* — Lynne Anderson
*Assistant Examiner* — Bradley Philips
(74) *Attorney, Agent, or Firm* — Lowe, Hauptman & Ham

(57) ABSTRACT

A disposable diaper is provided with an outer body including a belly side portion and a back side portion, and an inner body. The belly side portion and back side portion of the outer body each has a plurality of waist elastic members extending in parallel to each other in the transverse direction. The outer body has an annular waist gather region, a belly side pressing region, a back side pressing region, and an annular tightening region. The area of the back side pressing region is smaller than the area of the belly side pressing region, and the contractile force of the back side pressing region is smaller than the contractile force of the belly side pressing region, and is no greater than 0.35N, and the contractile force per unit width of the tightening region is no less than 0.45N/25 mm.

9 Claims, 6 Drawing Sheets

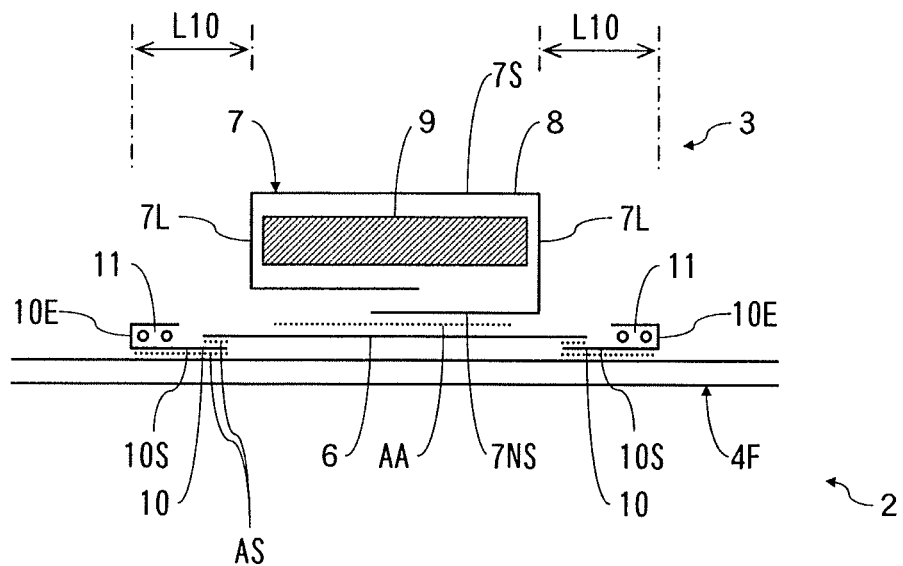
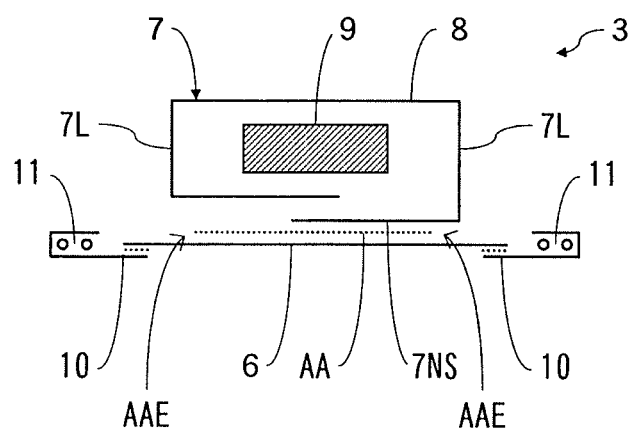

DISPOSABLE DIAPER

BACKGROUND OF THE INVENTION

1. Field of the Invention

This invention relates to a disposable diaper.

2. Related Art

When a diaper absorbs urine discharged by a wearer, the diaper may slide downward relative to the wearer as the diaper becomes heavier.

A disposable diaper which is configured so as not to slide downward due to the absorption of urine is known (refer to Japanese Unexamined Patent Publication (Kokai) No. 2007-29482).

SUMMARY OF THE INVENTION

In tropical or subtropic regions, such as in South East Asia or South Asia, due to high temperature and humidity, instead of being used throughout the day, a disposable diaper may only be used for a limited number of hours during the day, for instance, while a guardian, such as a mother, is busy with house chores, or during a daytime nap.

Therefore, in such a case, high absorption capability is not required for a diaper, and a diaper having relatively low absorption capacity is preferable. Manufacturing cost can be reduced when absorption capacity is low.

However, for a diaper with such a low absorption capacity, the guardian needs to know whether or not urination has occurred, or the appropriate timing of changing of a diaper, so as to prevent leakage.

On the other hand, in the above-mentioned regions, because of the above-mentioned climate, other clothes are not worn or only simple cloth underpants are worn over the diaper. Therefore, if a diaper appropriately slides downward relative to a wearer when the diaper absorbs urine, the guardian can easily see that the diaper needs to be changed.

Such a technical idea is not disclosed in JP'482, and is opposite of JP'482.

According to the present invention, there is provided a pants-type disposable diaper comprising an outer body including a belly side portion and a back side portion, an inner body comprising an absorbent including an absorption core, the belly side portion and the back side portion of the outer body being separated from each other and adjoined to each other at joint portions, the inner body being joined to the belly side portion and the back side portion of the outer body, to form a waist opening and a pair of leg openings, wherein each of the belly side portion and the back side portion of the outer body has a plurality of waist elastic members extending substantially parallel to each other in the transverse direction, the outer body has an annular waist gather region in the belly side portion and the back side portion extending from the upper end of the belly side portion to the upper end of the inner body on the belly side in the transverse direction, a band-shaped belly side pressing region in the belly side portion extending between the lower end of the belly side portion and the upper end of the absorption core on the belly side in the transverse direction, a band-shaped back side pressing region in the back side portion extending between the lower end of the back side portion and the upper end of the absorption core on the back side in the transverse direction, and an annular tightening region in the belly side portion and the back side portion extending between the lower end of the waist gather region and the upper end of the back side pressing region in the transverse direction, the area of the back side pressing region is smaller than the area of the belly side pressing region, the contractile force of the back side pressing region is smaller than the contractile force of the belly side pressing region, and is no greater than 0.35N, and the contractile force per unit width of the tightening region is no less than 0.45N/25 mm.

The present invention may be more fully understood from the description of the preferred embodiments according to the invention as set forth below, together with the accompanying drawings.

BRIEF DESCRIPTION OF THE DRAWINGS

In the drawings:

FIG. 2 shows a schematic sectional view taken along the line II-II in FIG. 1;

FIG. 3 shows a schematic sectional view taken along the line in FIG. 1;

DESCRIPTION OF THE PREFERRED EMBODIMENTS

Figure 1:
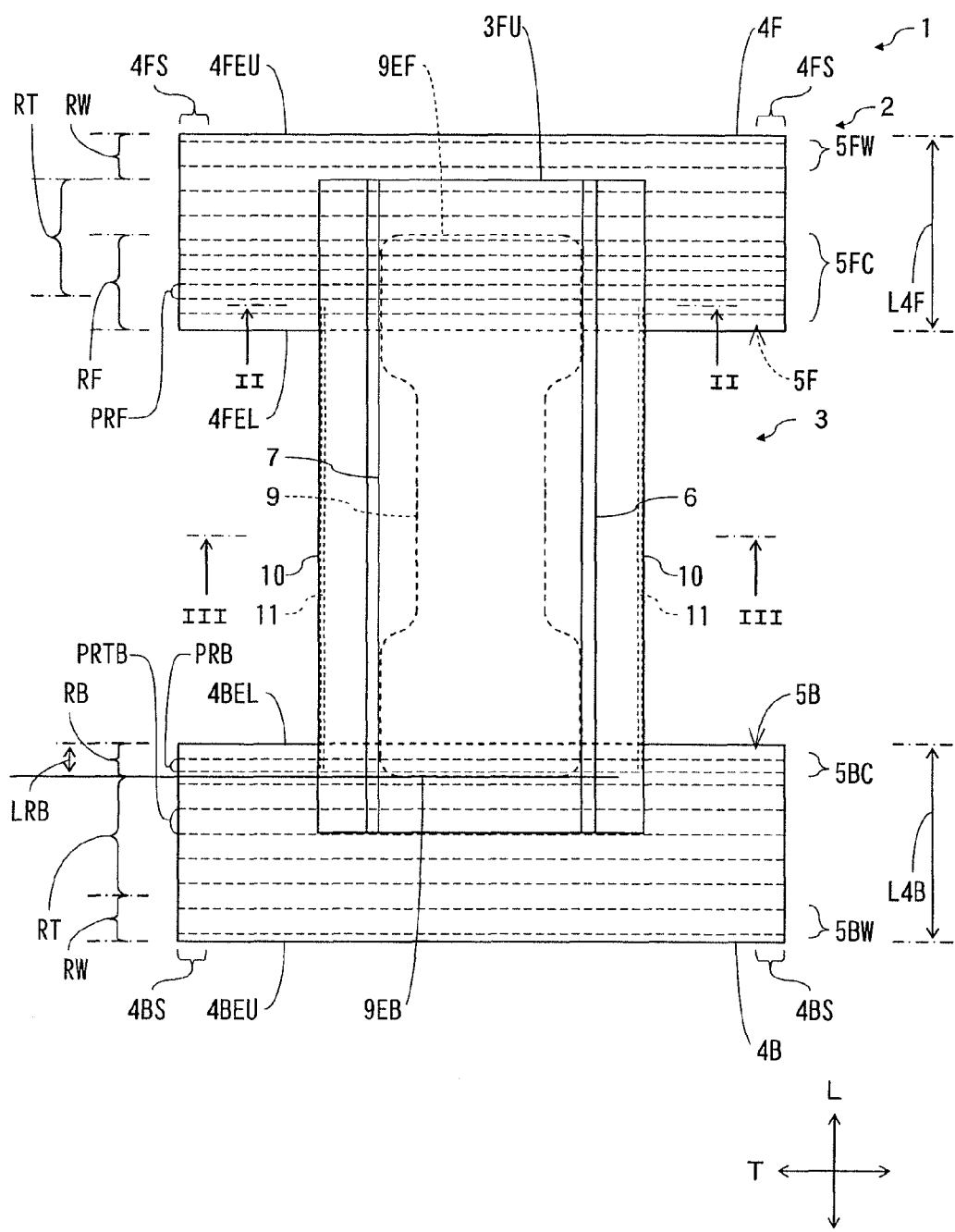
FIG. 1 shows a developed plan view of the disposable diaper.

With reference to FIGS. 1, 2, and 3, a disposable diaper 1 comprises an outer body 2 and an inner body 3. In FIG. 1, L indicates a longitudinal direction and T indicates a transverse direction perpendicular to the longitudinal direction.

The outer body 2 comprises a belly side portion 4F and a back side portion 4B. The belly side portion 4F and the back side portion 4B are located on the belly side and the back side of the wearer, respectively, when the diaper is worn by the wearer.

The belly side portion 4F and the back side portion 4B each has a rectangular shape, and are separately arranged in the longitudinal direction L. The belly side portion 4F and the back side portion 4B are provided with waist elastic members 5F, 5B, extending substantially parallel to each other in the transverse direction T, in a stretched state. Also, as shown in FIG. 2, each of the belly side portion 4F and the back side portion 4B comprises two-ply sheets, and the waist elastic members 5F, 5B are placed between these sheets.

The inner body 3 extends in the longitudinal direction L, is adjoined to the belly side portion 4F and the back side portion 4B, and is located at the crotch of the wearer when the diaper is worn.

The inner body 3 comprises a liquid-impermeable back sheet 6 and an absorbent 7 adjoined to the back sheet 6. As shown in FIG. 2, the absorbent 7 includes a liquid-permeable skin side sheet 8 and a liquid-retaining absorption core 9 enclosed by the skin side sheet 8. In this case, the skin contact side face of the absorption core 9 directly contacts with the skin side sheet 8, namely, no other sheet is provided between the skin contact side face of the absorption core 9 and the skin side sheet 8. Thus, the skin side sheet 8 also functions as a core wrap to wrap the absorption core 9. As a result, a core wrap and a second sheet, etc., can be omitted, and thus, the manufacturing cost of the diaper can be reduced to a large extent.

The back sheet 6 has a rectangular shape, and is made of materials, such as hydrophobic unwoven fabric, impervious plastic film, or a laminated sheet of unwoven fabric and impervious plastic film. The back sheet 6 may be breathable or non-breathable.

The skin side sheet 8 is made of a single rectangular sheet consisting of, for example, two spun bonded layers and a melt blown layer between the spun bonded layers. In this case, the weight per unit area of the entire skin side sheet 8, the spun bonded layers, and the melt blown layer can be set as $10 \text{ g/m}^2$, $8 \text{ g/m}^2$, $2 \text{ g/m}^2$, respectively. Also, the melt blown layer can be applied with hydrophilic oil. Further, the tensile strength of the skin side sheet 8 both in the longitudinal direction and in the transverse direction are, for example, $4.0 \text{ N/m}^2$ or greater, under either dry or wet condition. That is, the skin side sheet 8 has sufficient tensile strengths both in the longitudinal and transverse directions, under either dry or wet condition. Therefore, the leakage and slippage of the absorption core 9, specifically of the SAP particles, can be prevented when the core wrap is omitted. In addition, as the skin side sheet 8 includes a melt blown layer, the leakage and slippage of the SAP particles can be certainly prevented. At the same time, the skin of the wearer contacts the spun bonded layer of the skin side sheet 8, therefore, a comfortable feel in texture is obtained. Also, as the skin side sheet 8 contains a spun bonded/melt blown/spun bonded trilaminar structure, the handling thereof is easy.

The absorption core 9 is made of, for example, a fiber assembly and superabsorbent polymer particles. The fiber assembly consists of cellulose fibers such as a pulp fiber, a cotton fiber, or a rayon fiber, or synthetic fibers made of synthetic resins such as polyester/polyethylene. Superabsorbent polymer (SAP) particles consist of, for example, acrylic acid polymer or copolymer which can absorb and retain a liquid having a weight more than 15 times the weight of the polymer, and turn into a gel upon the retention of liquid.

Figure 4:
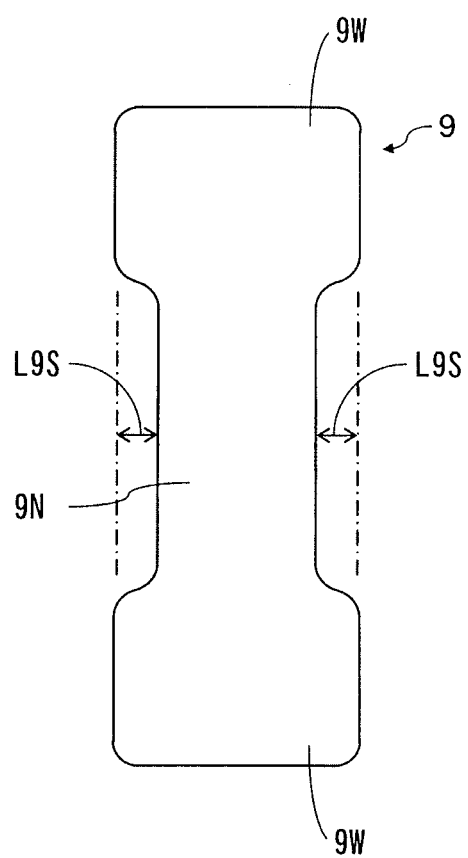
FIG. 4 shows a plan view of the absorption core.

As shown specifically in FIG. 4, absorption core 9 has wide portions 9W at both ends in the longitudinal direction and a narrow portion 9N located between the wide portions 9W. The absorption core 9 is shaped so that the distance L9S between the side ends of the wide portions 9W and the side ends of the narrow portion 9N in the transverse direction is not less than 15 mm, at both sides of the absorption core 9.

The absorbent 7 is formed so that the absorption capacity of the absorbent 7 is not more than 150 g. With such a structure, the amount of material required for forming the absorbent 7 can be reduced, and thus, the manufacturing cost can be reduced. Note that the absorption capacity of the absorbent 7 may be greater than 150 g.

The absorption capacity is calculated as below. First, the absorbent 7 is removed from the diaper 1 and is made as a sample. The sample is soaked in 2000 ml of saline for 30 minutes in a 250 mesh plastic bag, to let the SAP particles become sufficiently swollen. Next, the weight of the sample is measured, then, after removing the water by a centrifuge machine at 150 G, for two minutes, the sample is re-weighed. The absorption capacity is calculated by the following formula.

The absorption capacity(g)=(sample weight after water removal—sample weight before being soaked)

As shown specifically in FIGS. 2 and 3, a pair of leg sheets 10 extending from the side ends 7L, 7L of the absorbent 7 in the transverse direction are provided at the non-skin contact side face 7NS of the absorbent 7. In this case, the leg sheets 10 extend by L10 from the respective side ends 7L and 7L in the transverse direction.

Also, the leg sheet 10 is provided at each of the distal ends 10E with a leg elastic member 11 extending in the longitudinal direction in a stretched state. The leg sheet 10 is folded back on itself at the distal end 10E of the leg sheet 10 to hold the leg elastic members 11. In this case, the portion 10S of the leg sheet between the back sheet 6 and the leg elastic members 11 is made of a single layer sheet material which is not folded. That is, the leg sheet 10 is at least partially made of a single layer sheet material.

The leg sheet 10 is adjoined to the back sheet 6 and the outer body 2 by a hot-melt adhesive AS spread in the longitudinal direction L. Therefore, the leg sheet 10 has a portion to be adjoined to the outer body 2, without having a portion to be adjoined to the skin contact side face 7S of the absorbent 7.

Also, the back sheet 6 is adjoined to the non-skin contact side face 7NS of the absorbent 7 by a hot-melt adhesive AA spread in the longitudinal direction L. In this case, as shown in FIG. 3, side ends AAE, AAE of the hot-melt adhesive AA are located slightly more inside in the transverse direction than the side ends 7L and 7L of the absorbent 7, and therefore, extend in the longitudinal direction L on the non-skin contact side of the absorbent 7. When the diaper is worn, the leg sheets 10 are raised at respective side ends AAE and AAE of the hot-melt adhesive AA. That is, the side ends AAE and AAE form a pair of fixed-ends for raising of the leg sheet 10. Therefore, fixed-ends for raising of the leg sheets 10 extend in the longitudinal direction on the non-skin contact side of the absorbent 7.

Thus, the outer body 2 is provided with waist elastic members 5F and 5B in the transverse direction, and the inner body 3 is provided with leg elastic members 11 in the longitudinal direction. That is, in the embodiments of the present invention, the outer body 2 and the inner body 3 do not have elastic members in the direction crossing the transverse direction and the longitudinal direction, respectively. Note that the outer body 2 and the inner body 3 may have elastic members in the direction crossing the transverse direction and the longitudinal direction.

Figure 5:
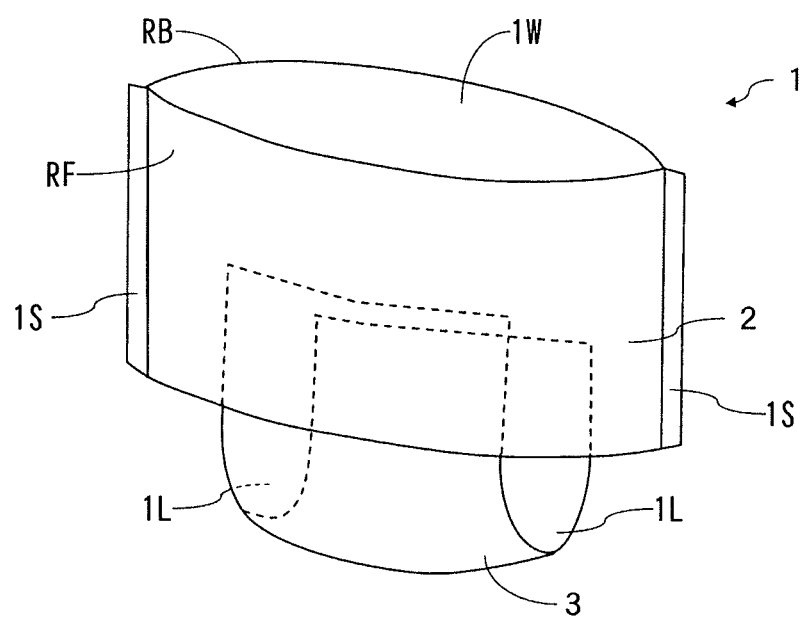
FIG. 5 shows a schematic perspective view of the diaper.

The back sheet 6 of the inner body 3 is adjoined to the belly side portion 4F and the back side portion 4B of the outer body 2 at the respective ends of the longitudinal direction of the back sheet 6. Also, the inner face of the side portion 4FS of the belly side portion 4F and the inner face of the side portion 4BS of the back side portion 4B are adjoined to each other to form a joint portion 1S. Thus, a pants-type disposable diaper 1 as shown in FIG. 5 is formed. This pants-type disposable diaper 1 includes a waist opening 1W and a pair of leg openings 1L.

In this case, the side portions 4FS and 4BS are joined to each other having the upper end 4FEU of the belly side portion 4F and the upper end 4BEU of the back side portion 4B being substantially aligned with each other. In the example of FIG. 1, the longitudinal length L4F of the belly side portion 4F and the longitudinal length L4B of the back side portion 4B are equal to each other, therefore, the lower end 4FEL of the belly side portion 4F and the lower end 4BEL of the back side portion 4B are substantially aligned with each other.

Referring to FIG. 1 once again, the outer body 2 has an annular waist gather region RW in the belly side portion 4F and the back side portion 4B extending from the upper end 4FEU of the belly side portion 4F to the upper end 3FU of the inner body 3 on the belly side in the transverse direction. The waist gather region RW includes elastic members 5FW and 5BW of the waist elastic members 5F and 5B.

The outer body 2 further includes a band-shaped belly side pressing region RF in the belly side portion 4F extending between the lower end 4FEL of the belly side portion 4F and the upper end 9EF of the absorption core 9 on the belly side in the transverse direction. The belly side pressing region RF includes elastic members 5FC of the waist elastic members 5F, and is pressed to the wearer by the elastic members 5FC when the diaper is worn.

The outer body 2 further includes a band-shaped back side pressing region RB in the back side portion 4B extending between the lower end 4BEL of the back side portion 4B and the upper end 9EB of the absorption core 9 on the back side in the transverse direction. The back side pressing region RB includes elastic members 5BC of the waist elastic members 5B, and is pressed to the wearer by the elastic members 5BC when the diaper is worn. In FIG. 1, LRB represents a longitudinal length of the back side pressing region RB, and is, for example, 20 mm.

Further, the outer body 2 includes an annular tightening region RT in the belly side portion 4F and the back side portion 4B extending between the lower ends RWE of the waist gather regions RW and the upper end RBU of the back side pressing region RB in the transverse direction.

In addition, the area of the back side pressing region RB is smaller than the area of the belly side pressing region RF. That is, in consideration that the transverse length of the back side pressing region RB and the transverse length of the belly side pressing region RF are almost equal to each other, the longitudinal length of the back side pressing region RB is smaller than the longitudinal length of the belly side pressing region RF. As a result, the back side pressing region RB tends to slide downward relative to the wearer, and the belly side pressing region RF tends to not slide downward.

Also, the contractile force of the back side pressing region RB is smaller than the contractile force of the belly side pressing region RF, and is no greater than 0.35 N. As a result, the back side pressing region RB tends to slide downward, and the belly side pressing region RF tends to not slide downward.

The contractile forces of the belly side pressing region RF and the back side pressing region RB are measured as follows. That is, a sample is prepared by removing the belly side pressing region RF and the back side pressing region RB together with the inner body 3 from the diaper 1. This sample comprises two-ply sheets, and waist elastic members 5F and 5B placed between these sheets. Then, the sample is spread out in the transverse direction to remove creases, and retained. At this initial stage, the waist elastic members 5F and 5B are in a stretched state. If the portion of the sample which can contact to the wearer's skin is referred to as a contact portion, then the transverse length of the contact portion, i.e., a distance of the two inner edges of the side portion 4FS in the transverse direction or a distance of the two inner edges of the side portion 4BS in the transverse direction is measured. The measurement is set as an initial value. Next, a tensile force (N) of the sample is measured by an autograph machine made by Shimadzu Corporation. Specifically, the sample is left in a natural state without applying a tensile force or contractile force. In this case, the sample is contracted from the above mentioned initial stage, and the transverse length of the contact portion of the sample is, for example, 40% of the initial value. Then, the sample is held by a pair of chucks. In this case, the sample is held so that the inner edge of the chucks matches the inner edges of the side portions 4FS and 4BS in the transverse direction, therefore, the contact portion is stretchably located between a pair of chucks. Next, the chucks are moved and stretch the sample so that the transverse length of the contact portion is 85% of the initial value. Then, the moving direction of the chucks is reversed and the sample is contracted at a speed of 100 mm/min so that the transverse length of the contact portion is 65% of the initial value. Then, the tensile force (N) of the sample at this point is measured, and this measured value is the contractile force of the sample.

It has been found that the transverse length of the above contact portion is around 65% of the initial value, when a wearer of an average size wears the diaper 1. Therefore, the tensile force when the transverse length of the contact portion is 65% of the initial value is obtained as the contractile force.

Further, the contractile force per unit width (25 mm) of the tightening region RT is no less than 0.45N/25 mm.

The contractile force per unit width is calculated as below. That is, a sample is prepared by removing the tightening region RT from the diaper 1, while the side portions 4FS and 4BS are adjoined to each other. Then, the tensile force of the sample is measured, in the same way as the measurement of the contractile force of the belly side pressing region RF and the back side pressing region RB described above. Next, the contractile force (N/25 mm) per unit width (25 mm) is calculated by multiplying the measured value of the tensile force by a coefficient (25/L4F). L4F is a longitudinal length L4F (mm) of the belly side portion 4F corresponding to the sample width (FIG. 1).

Also, the pitch PRTB of the elastic members 5B in the tightening region RT located in the back side portion 4B is greater than the pitch PRB of the elastic members 5B in the back side pressing region RB, and is 10 mm or greater. Further, the pitch PRF of the elastic members 5F in the belly side pressing region RF is smaller than the pitch PRB in the back side pressing region RB. With such a structure, the degree of freedom of the back side pressing region RB in the longitudinal direction L becomes high and the back side pressing region RB tends to slide downward relative to the wearer, this tendency is remarkable especially at the central portion in the transverse direction of the back side pressing region RB. In contrast, the degree of freedom of the belly side pressing region RF becomes low, and the belly side pressing region RF tends not to slide downward relative to the wearer.

In the embodiments of the present invention, the pitch PRTB is 14.5 mm, the pitch PRB is 7.5 mm, and the pitch PRF is 6.5 mm. Note that in an actual product, each pitch may have variations in errors of around ±0.5 mm.

Figure 6:
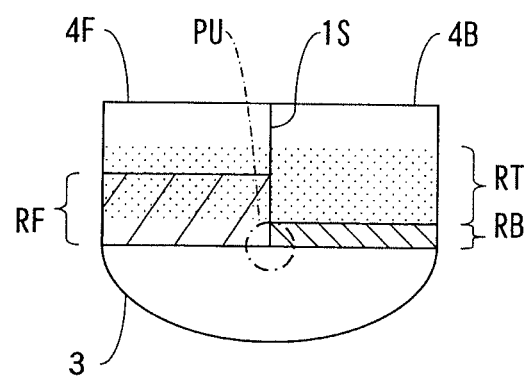
FIG. 6 shows a schematic side view of the diaper illustrating an embodiment of the present invention.

FIG. 6 is a schematic side view of the diaper 1 when worn and before urination occurs. The portion of the wearer's thigh joining the abdomen has a projection (great trochanter) of the femur, and the belly side pressing region RF and the back side pressing region RB abut against the upper portion PU of the projection or therearound. As a result, no downward sliding movement of the diaper 1 occurs.

Figure 7:
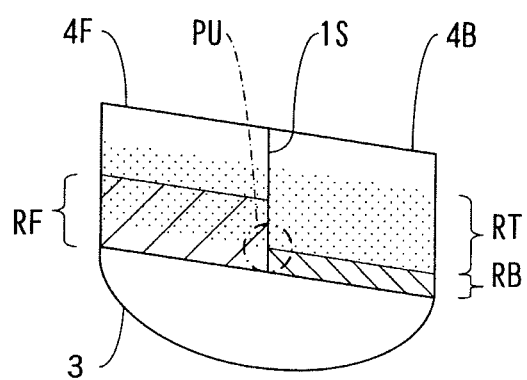
FIG. 7 shows a schematic side view of the diaper illustrating an embodiment of the present invention.

Next, when urination occurs, the urine is absorbed by the absorbent 7 or absorption core 9, and the diaper 1 becomes heavier. As described above, the back side pressing region RB tends to slide downward relative to the wearer. As a result, the back side portion 4B slides downward relative to the wearer, as shown in FIG. 7.

As a result, the appearance of the diaper 1 changes or walking may become more difficult for the wearer. In any case, the guardian such as a parent or the wearer will easily notice that urination occurred or that the diaper 1 needs to be changed.

Moreover, as the weight of the diaper 1, i.e., the amount of the urine absorbed by the diaper becomes greater, the displacement of the downward sliding movement of the back side portion 4B becomes greater. Therefore, the guardian will easily know the degree of necessity of changing the diaper 1 from the appearance of the diaper 1.

In contrast, the belly side portion 4F hardly slides downward relative to the wearer. Therefore, the belly side portion 4F or the belly side pressing region RF are maintained in close contact with the wearer. As a result, leakage can be prevented. Moreover, the downward sliding movement of the back side portion 4B is highlighted, and thus the guardian can easily notice the change in appearance of the diaper 1.

When the back side portion 4B slides downward, the tightening region RT located on the back side portion 4B abuts against the upper portion PU of the projection or therearound. As described above, the contractile force per unit width of the tightening region RT is made relatively greater. As a result, the further downward sliding movement of the back side portion 4B is prevented, therefore, the large downward sliding movement of the entire diaper 1 is prevented. In other words, the diaper 1 moderately slides downward.

In this case, if, for example, the absorption core 9 is tightly held on the crotch of the wearer, or the leg sheet 10 is adjoined to the skin contact side face 7S of the absorbent 7, the downward sliding movement of the diaper 1 may be restricted. The same is true for the cases wherein the absorbent 7 or the absorption core 9 are raised upward in the direction crossing the transverse direction and the longitudinal direction by the elastic members.

In contrast, in the embodiments of the present invention, as described above, the absorption core 9 is provided with a narrow portion 9N which is recessed by a relatively large distance L9S. Also, the leg sheet 10 is not adjoined to the skin contact side face 7S of the absorbent. In addition, the elastic members are not provided in the direction crossing the transverse direction and the longitudinal direction. Therefore, the diaper 1 can slide downward easily, and is prevented from sliding downward unintentionally.

Also, the rigidity of the leg sheet 10 is reduced by the portion 10s of the leg sheet made of a single layer sheet material, accordingly, the leg sheet 10 is easy to deform. Therefore, diaper 1 can slide downward easily with the leg sheet 10 being in contact with the leg of the wearer, i.e., with the leakage being prevented.

Further, when the diaper is worn, the leg sheet 10 is raised and abuts with the wearer's leg. As a result, leakage from the leg part can be prevented. In this case, the leg sheet 10 can be raised by the amount of extension L10 (FIG. 2).

Assuming that the back side portion 4B slides downward by the longitudinal length LRB of the back side pressing region RB, there is a possibility that a gap with a size of LRB is formed around the leg of the wearer, when the sliding occurs. Therefore, it is desirable that the amount of extension L10 is equal to or greater than LRB, so as to ensure the leakage prevention function of the leg sheet 10 when the downward sliding movement occurs. That is, in the embodiments of the present invention, as the longitudinal length LRB is 20 mm, it is desirable that the amount of extension L10 is no less than 20 mm.

Figure 8:
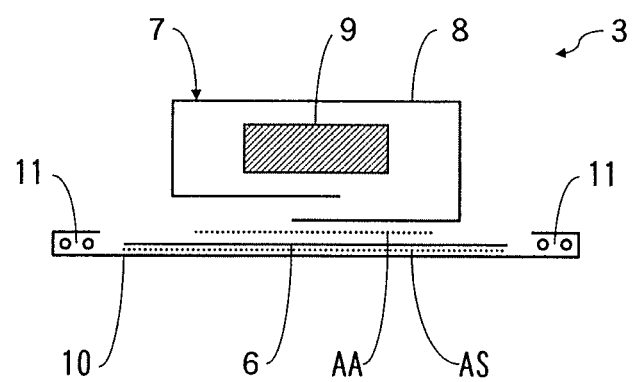
FIG. 8 shows a schematic sectional view of the diaper which is the similar to FIG. 3, illustrating another embodiment of the present invention.

In another embodiment shown in FIG. 8, a single leg sheet 10 is provided. Leg elastic members 11, 11 are held at both side ends of the leg sheet 10. Also, the entire back sheet 6 is covered by the leg sheet 10 and is adjoined to the leg sheet 10 by an adhesive AS.

Figure 9:
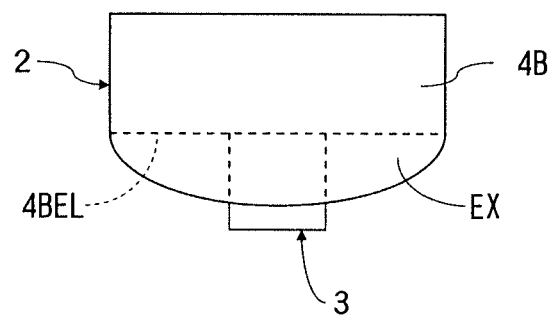
FIG. 9 shows a schematic rear view of the diaper illustrating another embodiment of the present invention.

In another embodiment shown in FIG. 9, an extension EX is provided extending downward from the lower end 4BEL of the back side portion 4B. With such a structure, the rear of the wearer can be hidden by the extension EX. The extension EX may or may not be provided with elastic members. Also, in the embodiment shown in FIG. 9, the extension EX is formed integrally with the back side portion 4B, but may be a separate member from the back side portion 4B.

EXAMPLES

As shown in Table 1, diapers 1 having different contractile force (N) of the back side pressing region RB, different contractile force (N) of the belly side pressing region RF, and different contractile force (N/25 mm) of the tightening region RT were prepared, as Examples 1 and 2, and a comparative example. For each diaper 1, the contractile force was measured five times and the lowest and the highest values are shown in Table 1.

|  | Contractile force (N) of the back side pressing region RB | Contractile force (N) of the belly side pressing region RF | Contractile force (N/25 mm) of the tightening region RT |
| --- | --- | --- | --- |
| Examples 1 | 0.20-0.27 | 0.82-0.92 | 0.50-0.65 |
| Examples 2 | 0.25-0.33 | 0.84-0.94 | 0.53-0.70 |
| Comparative example | 0.45-0.50 | 1.0-1.08 | — |

In each diaper 1, 80 ml of pseudo urine was absorbed by the absorbent 7. Then, the diaper 1 was worn by the wearer, and the appearance of the diaper 1 was observed as the first observation. Next, another 40 ml of pseudo urine was absorbed by the absorbent 7 (120 ml in total), and the diaper 1 was worn by the wearer and the change in the appearance of the diaper 1 was observed as the second observation.

In Examples 1 and 2, appearance changes of the diaper 1 were observed both in the first and the second observations. That is, the downward sliding movement of diaper 1 was observed. In the comparative example, a change in the appearance was not observed either in the first or the second observation.

The present invention can let a guardian or wearer know when it is time to change the diaper.

While the invention has been described by reference to specific embodiments chosen for purposes of illustration, it should be apparent that numerous modifications could be made thereto, by those skilled in the art, without departing from the basic concept and scope of the invention.

This application claims the benefit of UK Application No. 1018715.1, the entire disclosure of which is incorporated by reference herein.

The invention claimed is:

1. A pants-type disposable diaper having a longitudinal direction and a transverse direction transverse to the longitudinal direction, said disposable diaper comprising:
    an outer body including a belly side portion and a back side portion,
    an inner body comprising an absorbent including an absorption core,
    the belly side portion and the back side portion of the outer body being separated from each other and adjoined to each other at joint portions, the inner body being joined to the belly side portion and the back side portion of the outer body, to form a waist opening and a pair of leg openings, wherein
each of the belly side portion and the back side portion of the outer body has a plurality of waist elastic members extending substantially parallel to each other in the transverse direction,
each of the belly side portion and the back side portion includes an upper end facing the waist opening and a lower end opposing to the upper end in the longitudinal direction and facing the leg openings,
the outer body has
  a transversely extending annular waist gather region in the belly side portion and the back side portion, the transversely extending annular waist gather region in the belly side portion located between the upper end of the belly side portion to a belly side end of the inner body,
  a transversely extending band-shaped belly side pressing region in the belly side portion, the transversely extending band-shaped belly side pressing region in the belly side portion located between the lower end of the belly side portion and a belly side end of the absorption core,
  a transversely extending band-shaped back side pressing region in the back side portion, the transversely extending band-shaped back side pressing region in the back side portion located between the lower end of the back side portion and a back side end of the absorption core, and
  a transversely extending annular tightening region in the belly side portion and the back side portion, the transversely extending annular tightening region in the back side portion located between a lower end of the waist gather region and an upper end of the back side pressing region,
an area of the back side pressing region is smaller than an area of the belly side pressing region,
a contractile force of the back side pressing region is smaller than a contractile force of the belly side pressing region, and is no greater than 0.35N, and
a contractile force per unit width of the tightening region is no less than 0.45N/25 mm.

2. The disposable diaper according to claim 1, wherein
the upper ends of said belly side portion and said back side portion are substantially aligned to each other, and
a longitudinal length of the back side portion is equal to or greater than a longitudinal length of the belly side portion.

3. The disposable diaper according to claim 1, further comprising leg sheets extending from both side ends of the absorbent in the transverse direction, wherein the leg sheets are provided with leg elastic members on a non-skin contact side of said absorbent, and
the leg sheets have a portion adjoined to the outer body, and the leg sheets are not joined to a skin contact side of the absorbent.

4. The disposable diaper according to claim 3, wherein said leg elastic members are provided at distal ends of the leg sheets, and one of the leg sheets is at least partially made of a single layer sheet material.

5. The disposable diaper according to claim 3, wherein an amount of extension of one of said leg sheets from one of the side ends of said absorbent in the transverse direction is substantially equal to or greater than a longitudinal length of the back side pressing region.

6. The disposable diaper according to claim 3, wherein each of said leg sheets is adapted to be raised along respective fixed-ends of said leg sheet in use, and the fixed-ends extend in the longitudinal direction on the non-skin contact side of the absorbent.

7. The disposable diaper according to claim 1, wherein
a pitch of said waist elastic members in said tightening region located in said back side portion is greater than a pitch of the waist elastic members in said back side pressing region, and
a pitch of the waist elastic members in said belly side pressing region is smaller than the pitch of the waist elastic members in said back side pressing region.

8. The disposable diaper according to claim 1, wherein
said absorption core has wide portions opposing to each other in the longitudinal direction and a narrow portion located between the wide portions, and
a distance between side ends of the wide portions and side ends of the narrow portion in the transverse direction is not less than 15 mm, on both sides of the absorption core.

9. The disposable diaper according to claim 1, wherein a absorption capacity of the absorbent is not more than 150 g.

* * * * *